(12) United States Patent
Lapcevic

(10) Patent No.: US 6,840,923 B1
(45) Date of Patent: Jan. 11, 2005

(54) COLOSTOMY PUMP DEVICE

(75) Inventor: Milos Lapcevic, New South Wales (AU)

(73) Assignee: Colocare Holdings PTY Limited, New South Wales (AU)

( * ) Notice: Subject to any disclaimer, the term of this patent is extended or adjusted under 35 U.S.C. 154(b) by 296 days.

(21) Appl. No.: 10/018,887

(22) PCT Filed: Jun. 26, 2000

(86) PCT No.: PCT/AU00/00725

§ 371 (c)(1),
(2), (4) Date: Dec. 26, 2001

(87) PCT Pub. No.: WO01/00260

PCT Pub. Date: Jan. 4, 2001

(30) Foreign Application Priority Data

Jun. 24, 1999 (AU) .............................................. PQ1154

(51) Int. Cl.[7] .............................................. A61M 1/00
(52) U.S. Cl. ...................................... 604/319; 604/19
(58) Field of Search ........................ 604/317, 319–321, 604/327, 328, 332, 334, 335, 338, 355, 19, 28, 9.1, 313, 543

(56) References Cited

U.S. PATENT DOCUMENTS

| 4,413,994 | A | | 11/1983 | Sarashina | |
|---|---|---|---|---|---|
| 5,735,833 | A | * | 4/1998 | Olson | 604/289 |
| 5,788,683 | A | * | 8/1998 | Martin | 604/319 |
| 6,007,521 | A | * | 12/1999 | Bidwell et al. | 604/264 |
| 6,102,888 | A | * | 8/2000 | Walker | 604/28 |
| 6,315,755 | B1 | * | 11/2001 | Sussman | 604/28 |
| 6,319,222 | B1 | * | 11/2001 | Andrew et al. | 604/28 |
| 6,544,211 | B1 | * | 4/2003 | Andrew et al. | 604/28 |
| 6,585,720 | B2 | * | 7/2003 | Lapcevic | 604/540 |
| 6,595,971 | B1 | * | 7/2003 | von Dyck et al. | 604/334 |
| 2003/0060806 | A1 | * | 3/2003 | Ikeguchi | 604/540 |

FOREIGN PATENT DOCUMENTS

| EP | 0 744 179 A1 | * 11/1994 | ............ A61M/1/00 |
|---|---|---|---|
| WO | WO 96/14888 A1 | 5/1996 | |

* cited by examiner

Primary Examiner—Larry I. Schwartz
Assistant Examiner—M G Bogart
(74) Attorney, Agent, or Firm—Browdy and Neimark, P.L.L.C.

(57) ABSTRACT

A device for evacuating waste product through an orifice in a mammalian body, the device including a chamber having an irrigating means for introducing an irrigating fluid into the orifice and a suction means for removing the irrigating fluid waste products from the orifice.

35 Claims, 11 Drawing Sheets

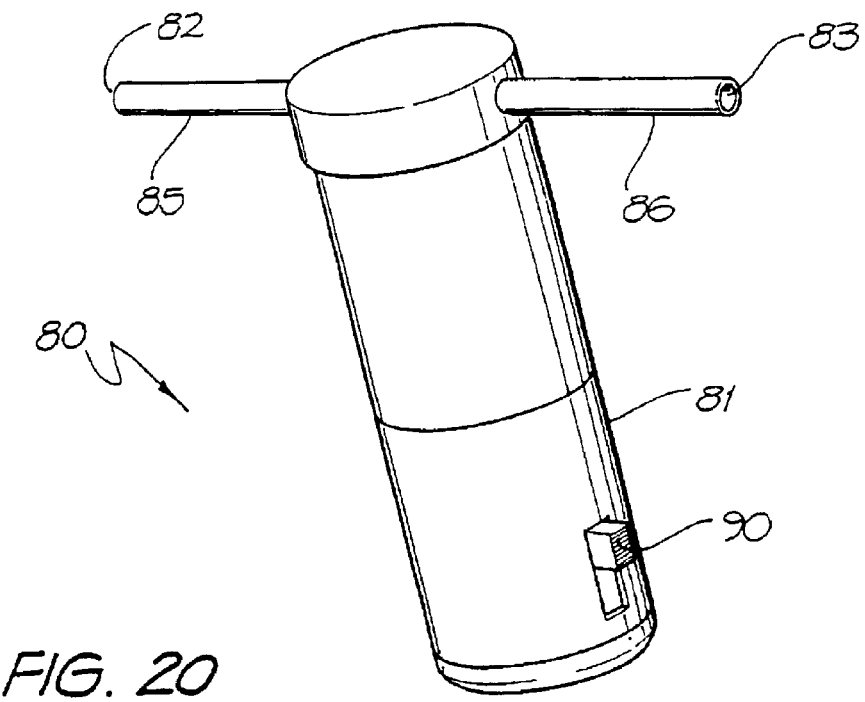
FIG. 20
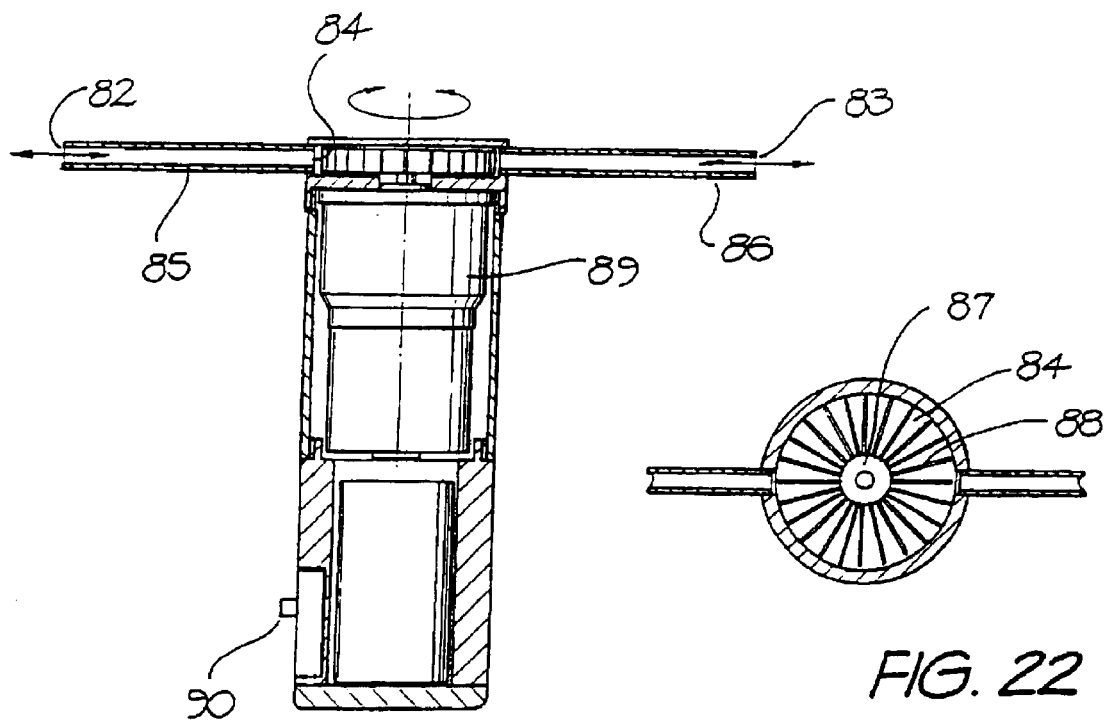
FIG. 21
FIG. 22

COLOSTOMY PUMP DEVICE

REFERENCE TO RELATED APPLICATIONS

The present application is the national stage under 35 U.S.C. 371 of international application PCT/AU00/00725, filed Jun. 26, 2000 which designated the United States, and which international application was published under PCT Article 21(2) in the English language.

FIELD OF THE INVENTION

The present invention relates to a device, system and method for evacuating waste product from bodily orifices, including stomas and in particular artificial stomas created as a result of surgical procedures, such as colostomies.

BACKGROUND OF THE INVENTION

The body has a number of natural stomas or openings, such as the anus, for passing waste product from within the body. Artificial stomas occasionally need to be provided to allow evacuation of waste products from within the body. One such stoma is the colostomy that is formed by bringing the conduit of the bowel to the body surface. In this case, faecal matter is normally made to pass through an orifice in the abdominal wall and into an adherent collection bag.

Artificial stomas are formed by surgical intervention and are typically required as a result of disease, congenital anomaly or injury. Of these, disease leads to the greatest number of operative procedures, with the main diseases being colonic cancer, Crohn's disease, ulcerative colitis and other inflammatory bowel diseases. Stoma care, therefore, is relevant to a significant percentage of the population.

As mentioned above, traditional methods of collecting faecal matter involves the adherence of a collection bag to the external surface of the abdomen. Such a method utilises an adhesive wafer or plate having an inlet opening for accommodating the stoma. The bag and wafer may form a disposable one-piece unit or alternatively a two-piece unit wherein the wafer remains adhered to the abdominal wall for several days and only the receiving bag is replaced. The service life of the wafer and the bag are to an extent dependent upon the amount of waste material but generally the adhesive wafer must be removed once it has become sufficiently deteriorated that faecal waste matter can come into contact with the skin surrounding the stoma. As such, wafers and bags typically have a service life of no greater than about two days.

Several problems are associated with the traditional wafer and bag devices such as skin irritations and infections due to faecal contamination and adverse reactions to the wafer adhesive. Indeed it is thought that up to 40% of stoma patients are affected by skin problems, this figure increasing to up to 80% in patients who have an ileostomy. Furthermore, the necessity to change the wafer and bag frequently seriously affects a patient's quality of life.

With the traditional methods, it has also been found that a certain amount of more fluid waste material has a tendency to collect at the entrance to the bag and thus removal of the bag may cause leakage of this material.

Moreover, the need to use the traditional wafer and collection bag devices imposes several problems for the ostomate, including restrictions to lifestyle (eg. poor utility, inconvenience, and need for dietary changes), psychological issues (eg. sexuality and poor self esteem) and an increased risk of herniation.

The introduction of irrigating liquid into the large intestine through the stoma can be used to stimulate faecal evacuation. One example of a device for introducing irrigating fluid that relies upon a gravity feed of the fluid into the intestine is described in U.S. Pat. No. 4,804,373. While describing a means of introducing an irrigating fluid, the device does not address many of the problems of the traditional wafer and bag systems.

A means of collecting waste material from the bowel of a patient is described in International Application No. PCT/AU97/00145. This application describes the use of a suction pump to aid evacuation of waste material from the bowel in place of the traditional adhesive bag method.

The present invention aims to provide a still further means of evacuating waste material which overcomes the problems associated with the traditional bag and wafer devices, improves the efficacy of traditional irrigation systems and suction systems such as described above.

SUMMARY OF THE INVENTION

According to a first aspect, the present invention consists in a device for evacuating waste product through an orifice in a mammalian body, the device including a chamber having an inlet and an outlet, the inlet being able to be brought into abutment with the body about the orifice and the outlet being connectable to a suction means, the device further including an irrigating means for introducing an irrigating fluid into the orifice, the irrigating means having a free end that is movable relative to the chamber between at least a first position outside the orifice and a second position at least partially within the orifice.

According to a second aspect, the present invention consists in a system for evacuating waste product through an orifice in a mammalian body, the system including a chamber having an inlet and an outlet, the inlet capable of being brought into abutment with the body about the orifice, a suction means that is connectable to the outlet and which can draw waste product at least from the chamber through the outlet, an irrigating means for introducing an irrigating fluid into the orifice, the irrigating means having a free end that is movable relative to the chamber between at least a first position outside the orifice and a second position at least partially within the orifice.

In one embodiment, the inlet of the chamber can seal with the body about the orifice. The inlet can be formed from a resiliently flexible material or a rigid material. For example, the inlet can be formed from a polymeric or elastomeric material. In another embodiment, the inlet can be substantially circular, however, other inlet shapes can be readily envisaged. The inlet of the chamber can include a bellow means that allows the inlet to deform on abutment with the body. For example, the bellow means can be formed from a silicone material. The inlet is preferably located at a first end of the chamber.

The outlet of the chamber is preferably located at a second end of the chamber distal the first end. The outlet preferably comprises an opening in the second end of the chamber. The opening is preferably surrounded by a spout extending outwardly from the second end and having a central bore in fluid communication with the opening. The spout preferably has an outer wall that tapers in diameter away from the second end. The spout is preferably detachably attachable to a pipe or tube that extends to or passes through a suction means. The tube or pipe preferably has a connector that allows relatively quick attachment of the tube or pipe to the spout by a user. The outlet of the suction means or of the pipe or tube passing through the suction means can direct the waste product directly into a toilet bowl or other suitable waste receptacle.

The second end of the chamber can be formed integrally with the chamber. In another embodiment, the second end can be formed separately and then mounted to the chamber. In one embodiment, the second end can have a skirt portion having a screw thread adapted to engage with a complementary screw thread on the container. The screw thread on the skirt portion can be on an inner or outer surface of the skirt portion, with the complementary screw thread on the outer or inner surface of the chamber, respectively. An O-ring can be located adjacent the screw thread between the skirt portion and the chamber to prevent waste product escaping from the chamber between the skirt portion and the wall of the chamber.

The second end can be formed from a material different to that of the chamber. As an example only, the second end can be formed from a polymeric material, such as nylon.

The chamber preferably has a further orifice formed therein to allow pressure equalisation between the interior and exterior of the chamber. The further orifice can be formed in a wall of the chamber or in the second end of the chamber. The further orifice can have an open-ended tube connected thereto. As a safety feature, and for ease of use, the further orifice is preferably adapted to be sealable by a finger of the user but could be closable or openable by other means. For example, the further orifice could be sealed by a pressure release valve or electronically actuated valve. Such a valve would vent the chamber should the pressure level within the chamber fall below some pre-set limit. The use of the further orifice in the chamber is described in more detail below.

The chamber can have a longitudinal axis and can be symmetrical or asymmetrical about this axis. The diameter of the chamber preferably decreases from the first end to the second end. In other embodiments, it can be envisaged that the chamber might increase in diameter from the first end to the second end or may be of a constant diameter along all or a portion of its length. Where the diameter of the chamber decreases in diameter away from the first end, the chamber can decrease in diameter relatively rapidly adjacent its first end and then decrease in diameter relatively slowly distal the first end. In another embodiment, the diameter can decrease relatively rapidly adjacent the first end and then remain at a constant diameter distal the first end. In a still further embodiment, the wall of the chamber can be substantially frusto-conical along at least a portion of its length.

The chamber can include at least one lug adapted to be connected to a belt, strap or other means of holding the chamber to the body of the user. In a preferred embodiment, the chamber has two oppositely disposed lugs at or adjacent its first end to which the respective ends of a belt are attached. In use, the belt is passed around the abdomen and is preferably adjustable or sufficiently elastic to hold the chamber in place against the body of the user.

Where the chamber has a screw thread complementary to a screw thread on the second end, the chamber is preferably substantially cylindrical in the region of the screw thread. The chamber can be formed from any suitable material. In one embodiment, the chamber can be formed from a readily cleanable material. The chamber can be formed from a transparent material to enable a user to watch the passage of the waste products through the chamber. As an example only, the chamber can be formed from a transparent polymethylmethacrylate (PMMA) material.

The irrigating means can comprise a catheter having at least one lumen in fluid communication with an orifice for the passage of an irrigating fluid therethrough. The catheter can extend through an opening in the second end of the chamber and preferably through an opening in the outlet of the chamber. In this embodiment, the catheter is relatively movable with respect to the second end but normally retains a substantial seal with the opening in the second end. An O-ring or grommet can extend around the catheter to maintain a seal between the catheter and the second end.

In another embodiment, the catheter can extend through the wall of the chamber rather than the second end. In this embodiment, the catheter is relatively movable with respect to the chamber wall but normally retains a substantial seal with the wall. An O-ring or grommet can extend around the catheter to maintain a seal between the catheter and the wall.

The catheter can be resiliently flexible along all or a portion of its length. A portion of the catheter adjacent its free end can be more rigid than the remainder of the catheter. In other embodiments, the region adjacent the free end can be less rigid or of the same rigidity as the remainder of the catheter.

The orifice of the lumen of the catheter is preferably at or adjacent its free end. In one embodiment, the orifice is in a sidewall of the catheter. In a still further embodiment, the catheter can have two or more orifices adjacent the free end.

The irrigating fluid normally utilised in conjunction with the device by a user will typically be water or a mixture including water. Stool softening agents such as liquid paraffin could be utilised.

The irrigating fluid can be forced through the catheter lumen by a pumping means that regulates the rate of flow of water through the catheter lumen. The pumping means can be manually or mechanically operated. The pumping means preferably provides fluid to the irrigating means at a pressure between about 1 and 5 psi. The pumping means can include a pressure release valve that is set to limit the fluid pressure in the irrigating means.

The pumping means can include a fluid meter that measures the quantity of fluid that has passed through the catheter lumen and allows this measurement to be read by the user. The fluid meter can also, if desired, provide a signal to shutdown or otherwise regulate operation of the pumping means once a predetermined quantity of fluid has passed through the catheter lumen. When used to pump fluid into a stoma of the large intestine, the pump may pump between about 1 and 1.5 liters of fluid through the irrigating means. The total quantity of fluid will be dependent on the length of large intestine of the ostomate and the needs of the ostomate. For example, on a particular day, less fluid may be required than on another day.

Where water is used, the water can be supplied from any normal water source, including a mains tap or a portable water container. Where warm water is unavailable and if desired by the user, a heating means can be employed to warm the water before it is pumped through the catheter lumen. Such a heating means can comprise an electrical heating element that is placed in the water container before the water is drawn from the container by the pumping means.

In a further embodiment, the catheter can have an orifice engaging member that is engagable with the wall of the orifice in the mammalian body when the catheter is in the second position relative to the chamber. In one embodiment, the orifice engaging member is an expandable member positioned adjacent its free end that can be expanded when the catheter is in the second position within the bodily orifice. The expandable member can comprise a balloon member that is inflatable by passing a fluid through the catheter to expand the balloon member. In a preferred embodiment, the balloon member is in fluid communication with a separate lumen within the catheter. When a small quantity of air or another fluid is injected into the separate lumen, the balloon member is caused to expand. When the air or other fluid is extracted, the balloon member deflates. The balloon is preferably expandable such that it substantially seals with the wall of the bodily orifice. In a preferred embodiment, the expansion of the balloon member occludes the bodily orifice about the catheter. The expansion of the balloon member within the bodily orifice also prevents relative movement of the catheter to the bodily orifice.

In another embodiment, the orifice engaging member can comprise a frusto-conical member that increases in diameter away from the free end of the catheter. The frusto-conical member can be formed from a polymeric or elastomeric material and serves to seal the orifice about the catheter when it is inserted into the orifice. The increasing diameter of the wall of the frusto-conical member serves to ensure that the catheter cannot be inadvertently inserted too far into the orifice.

In an alternative embodiment, the catheter can have a spacing member adapted to at least abut the body preferably about and immediately adjacent the bodily orifice when the catheter is in the second position. The spacing member can comprise a cup that is mounted to the catheter and spaced from its free end. The distance between the free end of the catheter and the spacing member sets the maximum depth of insertion of the free end into the bodily orifice. As the spacing member is mounted to the catheter it will be movable towards and away from the mammalian body as the catheter is so moved between its first and second positions. The cup can have a frusto-conical or cylindrical wall extending to a free end that is adapted to abut the body. The cup is preferably formed from a resiliently flexible polymeric or elastomeric material. If desired, the cup can be removable from the catheter and/or adjustable in position along the catheter. In normal use, the free end of the cup will be spaced from the free end of the catheter by a distance of between about 1 and 5 cm.

In a still further embodiment, the first end of the chamber can have an orifice engaging means that is insertable within the bodily orifice. In a preferred embodiment, the orifice engaging means is preferably expandable from a collapsed condition, so that the engaging means can be inserted into the orifice, to an expanded condition where the engaging means engages with the wall of the bodily orifice. In one embodiment, the engaging means can comprise an articulated jaw member that can be readily adjusted from the collapsed condition to the expanded condition and back to the collapsed condition. The jaw member can be encased within a substantially cylindrical and non-rigid sleeve that is movable into abutment with the wall of the bodily orifice on articulation of the jaw member into its expanded condition. The degree of expansion of the jaw member is preferably variable to allow the device to be positioned within bodily orifices of varying diameters. The sleeve can be formed from a silicone material.

The combination of the jaw member, when in the expanded condition, and the sleeve preferably defines a tubular area that extends outwardly from within the bodily orifice and is in fluid communication with the interior of the chamber.

The present device and system can be used to evacuate waste product through any suitable bodily orifice. It does, however, have particular application in the evacuation of waste product from natural and artificial stomas and, more particularly, colostomies.

According to a third aspect, the present invention consists in a device for evacuating waste product through an orifice in a mammalian body, the device including a chamber having an inlet and an outlet, the inlet being able to be brought into abutment with the body about the orifice and the outlet being connectable to a suction means, and an orifice engaging means that is insertable within the bodily orifice when the inlet of the chamber is in abutment with the body.

According to a fourth aspect, the present invention consists in a system for evacuating waste product through an orifice in a mammalian body, the system including a chamber having an inlet and an outlet, the inlet being able to be brought into abutment with the body about the orifice, a suction means that is connectable to the outlet and which can draw waste product at least from the chamber through the outlet, and an orifice engaging means that is insertable within the bodily orifice when the inlet of the chamber is in abutment with the body.

In one embodiment of the third or fourth aspects, the orifice engaging means is expandable from a collapsed condition to an expanded condition. When in the collapsed condition, the orifice engaging means is insertable within the bodily orifice. When in the expanded condition, the engaging means, when in the bodily orifice, preferably engages with the wall of the bodily orifice.

The engaging means can comprise an articulated jaw member that can be readily adjusted from the collapsed condition to the expanded condition and back to the collapsed condition. The jaw member can be encased within a non-rigid and preferably substantially cylindrical sleeve that is movable into abutment with the wall of the bodily orifice on articulation of the jaw into its expanded condition. The sleeve in one embodiment can be formed from a silicone material. The combination of the jaw member when in the expanded condition and the sleeve preferably defines a substantially tubular area that extends outwardly from within the bodily orifice and is in fluid communication with the interior of the chamber.

In the third and fourth aspects, the combination of the jaw member and the sleeve acts as both a means of delivering an irrigating fluid to within the bodily orifice and an outlet for waste exiting the orifice.

The irrigating fluid preferably enters the chamber through a fluid inlet in the chamber. The fluid inlet is preferably disposed in a wall of the chamber. The fluid inlet means is in turn preferably in fluid communication with a pipe or tube connected to a fluid source. The irrigating fluid normally utilised by a user of the device will typically be water or a mixture including water. The water can be supplied from any normal suitable water source, including a mains tap or a portable water container. If desired, a heating means can be employed to warm the water to a suitable temperature before it enters the fluid inlet in the chamber. Other stool softening agents, such as liquid paraffin could be utilised in conjunction with the device.

A pumping means can be used to pump the fluid into the chamber. The pumping means can be manually or mechanically operated. The pumping means preferably provides fluid to the fluid inlet at a pressure between about 1 and 5 psi. The pumping means can include a pressure release valve that is set to limit the fluid pressure in the chamber.

The pumping means can include a fluid meter that measures the quantity of fluid that has passed through the fluid inlet and allows this measurement to be read by the user. The fluid meter can also, if desired, provide a signal to shutdown or otherwise regulate operation of the pumping means once a predetermined quantity of fluid has passed through the fluid inlet. When used to pump fluid into a stoma of the large intestine, the pump may pump between about 1 and 1.5 liters of fluid through the fluid inlet. The total quantity of fluid will be dependent on the length of large intestine of the ostomate and the needs of the ostomate. For example, on a particular day, less fluid may be required than on another day.

In a further embodiment, a valve can be disposed in the outlet of the chamber. The valve is preferably movable between at least a first position where the outlet is closed and at least a second position where the outlet is open. The valve is preferably readily manually operable by the user of the device but could be adapted to open automatically at regular or irregular intervals.

In one embodiment of the third and fourth aspects, the inlet of the chamber can seal with the body about the orifice. The inlet can be formed from a resiliently flexible material to assist this sealing. For example, the inlet can be formed from a polymeric or elastomeric material. In another embodiment, the inlet can be substantially circular, however, other inlet shapes can be readily envisaged. The inlet of the chamber can include a bellow means that allows the inlet to deform on abutment with the body. In one embodiment, the bellows can be formed of a silicone material. The inlet is preferably located at a first end of the chamber.

The outlet of the chamber in the third and fourth aspects is preferably located in a second end of the chamber distal the first end. The outlet preferably comprises an opening in the second end of the chamber. The opening is preferably surrounded by a spout extending outwardly from the second end and having a central bore in fluid communication with the opening. The spout preferably has an outer wall that tapers in diameter away from the second end. The spout is preferably detachably attachable to a pipe or tube that extends to or passes through a suction means. The tube or pipe preferably has a connector that allows relatively quick attachment of the tube or pipe to the spout by a user.

The second end of the chamber in the third and fourth aspects can be formed integrally with the chamber. In another embodiment, the second end can be formed separately and then mounted to the chamber. In one embodiment, the second end can have a skirt portion having a screw thread adapted to engage with a complementary screw thread on the container. The screw thread on the skirt portion can be on an inner or outer surface of the skirt portion, with the complementary screw thread on the outer or inner surface of the chamber, respectively. An O-ring can be located adjacent the screw thread between the skirt portion and the chamber to prevent waste product escaping from the chamber between the skirt portion and the wall of the chamber.

The second end of the device in the third and fourth aspects can be formed from a material different to that of the chamber. As an example only, the second end can be formed from a polymeric material, such as nylon.

The chamber preferably has a further orifice formed therein to allow pressure equalisation between the interior and exterior of the chamber. The further orifice can be formed in a wall of the chamber or in the second end of the chamber. The further orifice can have an open-ended tube connected thereto. The further orifice is preferably adapted to be sealable by a finger of the user but could be closable by other means. For example, the further orifice could be sealed by a pressure release valve. Such a valve could vent the chamber should the pressure level within the chamber fall below some pre-set limit.

The chamber in the third and fourth aspects can have a longitudinal axis and can be symmetrical or asymmetrical about this axis. The diameter of the chamber preferably decreases from the first end to the second end. In other embodiments, it can be envisaged that the chamber might increase in diameter from the first end to the second end or may be of a constant diameter along all or a portion of its length. Where the diameter of the chamber decreases in diameter away from the first end, the chamber can decrease in diameter relatively rapidly adjacent its first end and then decrease in diameter relatively slowly distal the first end. In another embodiment, the diameter can decrease relatively rapidly adjacent the first end and then remain at a constant diameter distal the first end. In a still further embodiment, the wall of the chamber can be substantially frusto-conical along at least a portion of its length.

The chamber can include at least one lug adapted to be connected to a belt, strap or other means of holding the chamber to the body of the user. In a preferred embodiment, the chamber has two oppositely disposed lugs at or adjacent its first end to which the respective ends of a belt are attached. In use, the belt is passed around the abdomen and is preferably adjustable or sufficiently elastic to hold the chamber in place against the body of the user.

Where the chamber has a screw thread complementary to a screw thread on the second end, the chamber is preferably substantially cylindrical in the region of the screw thread. The chamber can be formed from any suitable material. In one embodiment, the chamber can be formed from a readily cleanable material. The chamber can be formed from a transparent material to enable a user to watch the passage of the waste products through the chamber. As an example only, the chamber can be formed from a transparent polymethylmethacrylate (PMMA) material.

The device and system of the third and fourth aspects, respectively, can be used to evacuate waste product through any suitable bodily orifice. It does, however, have particular application in the evacuation of waste product from artificial stomas and, more particularly, colostomies. The device can also be used to draw waste from the anus in the case where the user is suffering from chronic constipation. In this case, the device might be mounted in an appropriate way to a modified toilet seat to allow the user to sit comfortably on the toilet before using the device. The outlet of the suction means in this case could direct the waste product directly into the toilet bowl before the toilet is flushed in the usual manner.

In the above aspects, the device and/or system can comprise a portable device. Where a powered pumping means and/or suction means are utilised, the power for these devices can be provided by a battery. The battery is preferably rechargeable and portable along with the device. The device along with at least its pumping means, suction means and power source can preferably be carried in a case.

According to a further aspect, the present invention comprises a toilet having a seat, the seat having mounted thereto the device according to the third aspect of the present invention.

According to a still further aspect, the present invention comprises a toilet incorporating the system according to the fourth aspect of the present invention.

In a particularly preferred embodiment of all of the above aspects, the suction means and irrigating fluid pumping means used in association with the waste evacuator devices defined herein comprise the same device, collectively defined hereafter as "the pump". In the device and system of the third and fourth aspects, respectively, the pump in this case serves to force fluid into the irrigating means of the device and also provides the necessary suction to the outlet of the chamber. In the device and system of the second and third aspects, respectively, the pump serves to force fluid into the chamber through the fluid inlet and also provides the suction to the outlet of the chamber.

In one embodiment, the pump can comprise a dual-action peristaltic type pump. In such a pump, the pipe connecting an irrigating fluid source to the irrigating means or fluid inlet and the pipe connecting the outlet of the chamber to a waste collection means each pass through a housing of the pump. By retaining the irrigating fluid and the waste product in separate tubes, the interior of the pump is kept clean and so does not need to be cleaned after each use as would be the case with normal pumps.

The dual-action peristaltic pump preferably incorporates one or more rollers adapted to be forced along a length of the pipes passing through the pump and so force the contents of the pipes along that length of the pipes. In a preferred embodiment, the rollers are mounted on a disc adapted to rotate within the housing. On rotation of the disc, the rollers compress the pipes that are mounted between the rollers and an outer wall of the housing. The rotation of the disc is preferably provided by a central drive shaft that is rotated by a motor in the housing. The motor can be mains powered or be powered by a battery.

While the suction means and pumping means can be a single pump means as defined above, it will be envisaged that separate devices could be utilised to provide these components of the systems according to the present invention. For example, manually and mechanically operable piston-type and impeller-type pumps could be utilised as suction means to draw waste product from the chamber. Individual peristaltic pumps could also be utilised to both force irrigating fluid through the irrigating means and draw waste product from at least the chamber.

Whichever type of pump is utilised in association with the device or in the systems defined herein, the pump will operate to provide suction within medically and regulatory approved ranges. The housing and componentry of the pumps can be constructed of any suitable material, such as polytetrafluoroethylene (PTFE).

According to a further aspect, the present invention consists in a method of evacuating waste product from an orifice in a mammalian body using the device according to the first aspect of the present invention.

According to a still further aspect, the present invention consists in a method of evacuating waste from an orifice in a mammalian body using the system according to the second aspect of the present invention, the method including the steps of:

(i) abutting the inlet of the chamber to the body about the orifice;

(ii) moving the irrigating means to the second position where its free end is at least partially within the orifice;

(iii) irrigating the bodily orifice with an irrigating fluid transported through the irrigating means; and (iv) applying suction to the outlet of the chamber to withdraw waste from the orifice into the chamber and through the outlet.

In a preferred embodiment, the method includes after step (ii) an additional step of engaging the free end of the irrigating means with the bodily orifice prior to and preferably at all times while the bodily orifice is irrigated with the irrigating fluid. The additional step can further include forming a sealing engagement between the free end of the irrigating means and the wall of the bodily orifice. By sealing the orifice around the irrigating means, the irrigating fluid that enters the bodily orifice is retained within the bodily orifice until such time as the seal is removed. The sealing engagement of the free end can be provided by an inflatable balloon that occludes the orifice around the irrigating means. The irrigating means can be sealingly engaged with the wall of the bodily orifice for a period of time between about a few minutes and about a few hours, more preferably between about 5 minutes and about 2 hours, still more preferably between about 10 and about 30 minutes.

In the above aspect, suction can be applied to the second end of the chamber either after the step of irrigating the bodily orifice has commenced or is completed or before, during and after the step of irrigating the bodily orifice. Optimal functioning of the present invention may be different for each user depending upon comfort, physiology and experience, with steps (ii), (iii) and (iv) being utilised in different sequences and for different lengths of time by different users and by the same user but at different times.

While suction is being applied to the second end of the chamber, the further pressure equalisation orifice in the chamber is normally sealed by the user by placing a finger over the further orifice. As soon as the finger is removed from the further orifice, the air pressure in the chamber is equalised with that outside the chamber. The pressure equalisation orifice thereby provides a ready means for the user to control the degree of suction applied to the chamber.

This method has particular application to the evacuation of waste product from artificial stomas, such as colostomies. The method can, however, also be utilised to gently evacuate waste product from natural stomas, such as the anus. In a preferred embodiment, the method of using the defined system is operable by the user without assistance.

According to a further aspect, the present invention consists in a method of evacuating waste product from an orifice in a mammalian body using the device according to the third aspect of the present invention.

According to yet a further aspect, the present invention consists in a method of evacuating waste from an orifice in a mammalian body using the system according to the fourth aspect of the present invention, the method including the steps of:

(i) abutting the inlet of the chamber to the body about the orifice;

(ii) engaging the orifice engaging means within the orifice;

(iii) irrigating the bodily orifice with an irrigating fluid; and (iv) applying suction to the outlet of the chamber to withdraw waste from the bodily orifice into the chamber and through the outlet.

In a preferred embodiment of this aspect, the orifice engaging means is preferably expandable from a collapsed condition to an expanded condition. When in the collapsed condition, the orifice engaging means is insertable within the bodily orifice. Once inserted, the engaging means is preferably expanded into engagement with the wall of the bodily orifice.

In a preferred embodiment, the irrigating fluid enters the chamber through a fluid inlet in the chamber before passing into the bodily orifice. The step of applying suction to the outlet of the chamber can commence once the inlet of the chamber is brought into abutment with the body and can be retained throughout use of the system. In another embodiment, suction is only applied to the outlet at certain times during use of the system.

In one particular embodiment, a valve can be disposed in the outlet of the chamber. The valve is preferably movable between at least a first position where the outlet is closed and at least a second position where the outlet is open. The valve is preferably readily manually operable by the user of the device but could be adapted to open automatically at regular or irregular intervals. In those cases where the valve is opened, suction will be applied to the entire chamber and preferably into the bodily orifice. When the valve is closed, continuous suction will not be provided to the entire chamber. In use, the valve can be periodically opened by the use to allow the evacuation of waste product from the chamber.

This method has particular application to the evacuation of waste product from artificial stomas, such as colostomies. The method can, however, also be utilised to gently evacuate waste product from natural stomas, such as the anus. In a preferred embodiment, the method of using the defined system is operable by the user without assistance.

BRIEF DESCRIPTION OF THE DRAWINGS

By way of example only, preferred embodiments of the invention are now described with reference to the accompanying drawings, in which:

FIG. 20 is a perspective view of another pump for use with the present invention;

FIG. 21 is a vertical sectional view of the pump of FIG. 20; and

FIG. 22 is a horizontal sectional view of the pump of FIG. 20.

PREFERRED MODE OF CARRYING OUT THE INVENTION

Figure 1:
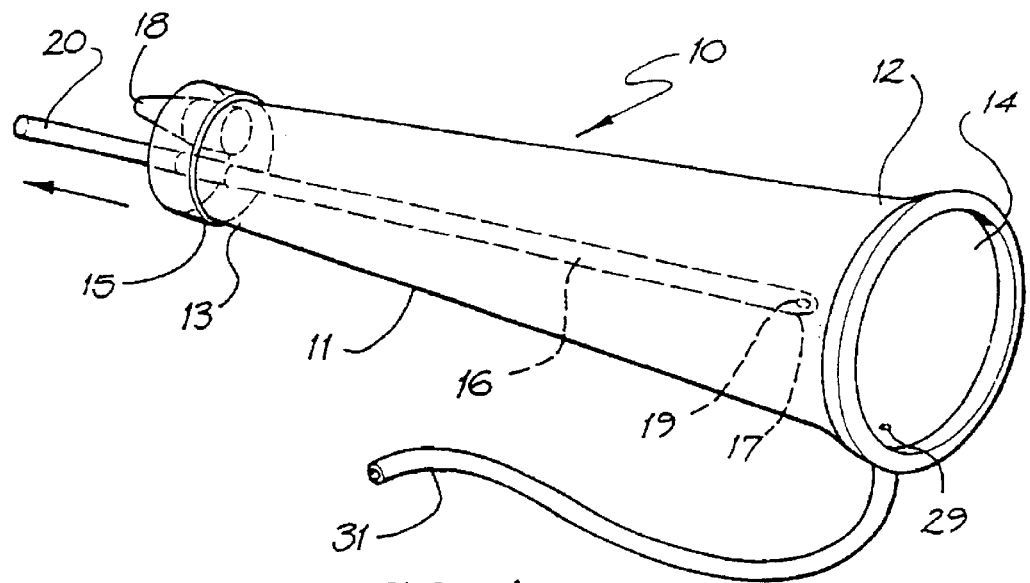
FIG. 1 is a perspective view of one embodiment of the invention with the irrigating catheter shown in a first position.

One embodiment of a device according to the present invention is generally depicted as 10 in the drawings. The device 10 is used in a system for evacuating waste product from the intestine of a user through an orifice such as a colostomy or ileostomy.

Figure 11:
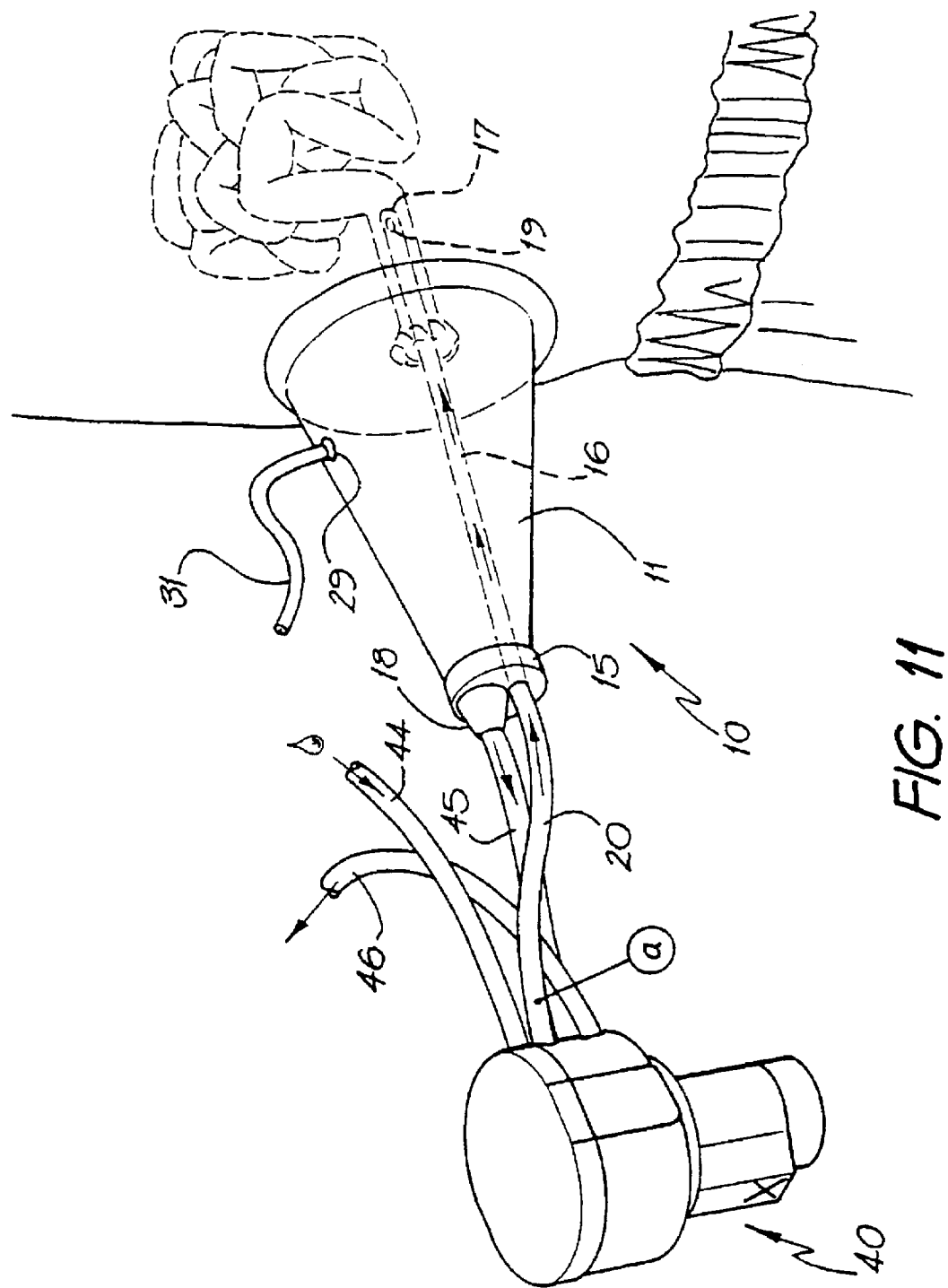
FIG. 11 illustrates one use of one embodiment of the device according to the present invention.

The device 10 comprises a main chamber 11 having a first end 12 and a second end 13. An inlet 14 to the main chamber 11 is located at first end 12 and an outlet 15 located at second end 13. In the depicted embodiment, outlet 15 is screwed onto the second end 13. It will be appreciated that the outlet 15 can be formed integrally with second end 13. The device 10 further includes an irrigating tube 16 which has a free end 17 that can be inserted into the orifice of the user and another end 20 adapted to sealably pass through outlet 15. End 20 may be connected to further tubing and extend to a water source such as a tap or a portable container. As depicted in FIG. 11, a pump 40 (as described below) can be used to force the water through irrigating tube 16.

Figure 2:
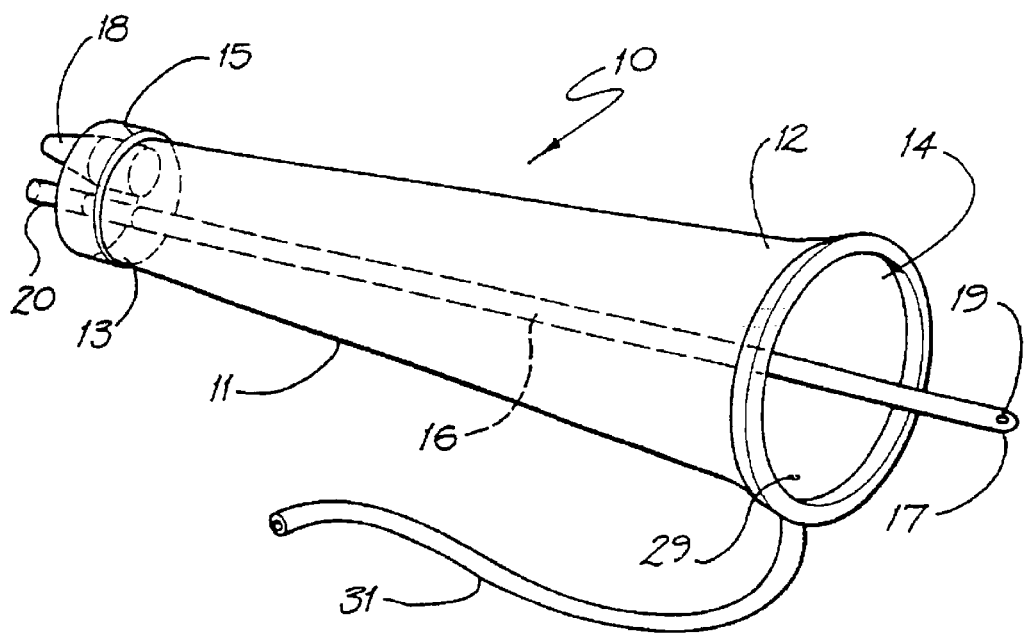
FIG. 2 is a perspective view of the embodiment of the invention depicted in FIG. 1 but with the irrigating catheter shown in a second position.

In use, the inlet 14 is placed against the skin of the user about the stoma or other bodily orifice and air drawn out of the main chamber 11 through a funnel 18 attached to or integral with outlet 15. The withdrawal of air from the main chamber 11 is facilitated by way of a suction pump attached to funnel 18 via a tube. Once a small quantity of air is evacuated from the main chamber 11, the inlet 14 forms a suction seal with the skin surrounding the orifice of the user. The free end 17 of the irrigating tube 16 is then moved into the orifice such that it is positioned internal the intestine of the user. It is envisaged that the free end 17 will extend relative to the inlet 14 a distance similar to that depicted in FIG. 2. The other end 20 of the irrigating tube 16 is connected to the water source and, once free end 17 is in place within the intestine, water is forced at a suitable pressure through the irrigating tube 16. The water is expelled from irrigating tube 16 through an aperture 19 or a series of apertures located at free end 17 and into the intestine. Typically, around 1–2 liters of water can be introduced into the intestine in this way. It is envisaged that in a preferred embodiment of the invention, the water is not introduced in one step. A user may introduce a preliminary volume of water, say, 0.5 liters at first instance and add the remaining volume of water at varying time intervals thereafter. In this embodiment, the introduction of the preliminary volume of water has the advantage of stimulating the intestine to contract thereby aiding the natural process of evacuation of waste from the intestine. Once the required volume of water has been introduced into the intestine, the irrigating tube 16 is retracted from the intestine of the user and into the main chamber 11, as depicted in FIG. 1.

As mentioned above, the water introduced into the intestine of the user stimulates a reflex contractile response in the intestine in addition to the process of irrigation which causes the water and any waste material in the intestine of the user to be dispelled. The water and waste material pass down through the intestine to the location of the orifice, through the orifice and into the main chamber 11 of device 10. Once the waste is in the main chamber 11, it flows towards second end 13 and ultimately is drawn through outlet 15 via funnel 18 due to the suction provided by the suction pump. During this process, it may assist a user to continue to force water through irrigating tube 16 when it is retracted into the main chamber. In this way the continuing flow of water acts in a flushing manner further facilitating removal of the waste material from main chamber 11.

Figure 3:
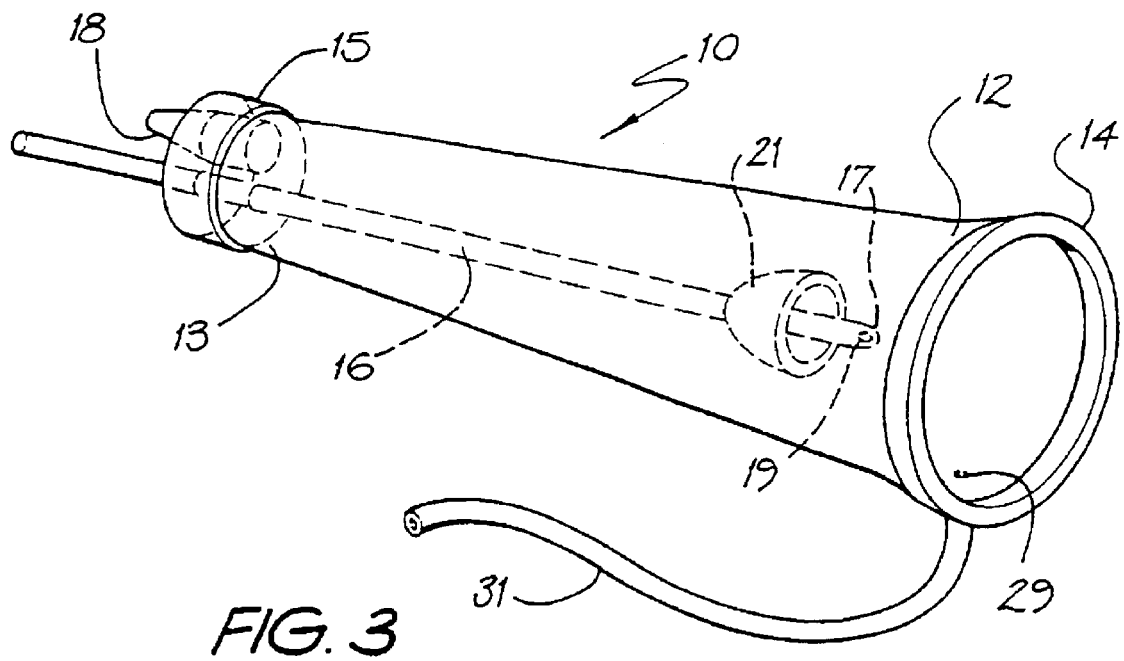
FIG. 3 is a perspective view of a second embodiment of the invention with the irrigating catheter shown in a first position.
Figure 4:
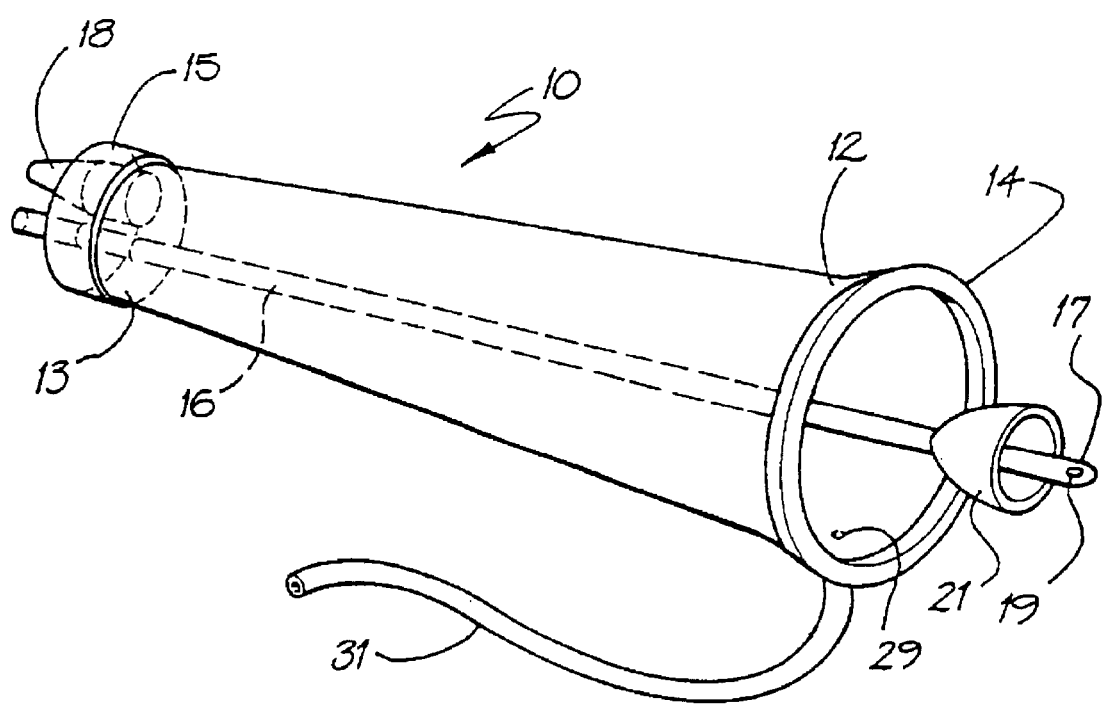
FIG. 4 is a perspective view of the embodiment of the invention depicted in FIG. 3 but with the irrigating catheter shown in a second position.

In another embodiment of the invention, depicted in FIGS. 3 and 4, the irrigating tube 16 is provided with a spacing cup 21 adjacent free end 17. In FIG. 4, for the purposes of clarity, the spacing cup 21 is depicted as extending outwardly of inlet 14 but in actual use is more in alignment with inlet 14 such that it abuts with the skin surrounding an orifice, such as a colostomy. The spacing cup 21 may be attached to or integral with the irrigating tube 16 and is preferably made from a resiliently flexible polymeric or elastomeric material. The spacing cup 21 may be movable relative free end 17 and the position of the spacing cup 21 from free end 17 dictates the distance that the irrigating tube 16 will enter the intestine. By abutting against the skin of a user, the spacing cup 21 prevents or at least substantially prevents leakage of water from the irrigating tube 16 in addition to preventing relative movement of the irrigating tube 16 to the bodily orifice.

In this embodiment, the inlet 14 is again placed against the skin of the user about the colostomy or other bodily orifice and air drawn out of the main chamber 11 through a funnel 18 attached to or integral with outlet 15. The withdrawal of air from the main chamber 11 is facilitated by way of a suction pump attached to funnel 18. Once a small quantity of air is evacuated from the main chamber 11, the inlet 14 forms a suction seal with the skin surrounding the orifice of the user. The withdrawal of air from main chamber 11 also causes the spacing cup 21 to form a suction seal with the skin surrounding the bodily orifice. Once inlet 14 is in position, the free end 17 of the irrigating tube 16 is then moved into the bodily orifice a distance set by the distance of the spacing cup 21 from the free end of the tube such that it is positioned internal the intestine of the user. It is envisaged that the free end 17 will extend relative to the inlet 14 a distance similar to that depicted in FIG. 4. The other end 20 of the irrigating tube 16 is again connected to a water source and, once free end 17 is in place within the intestine, water is forced through the irrigating tube 16 at a suitable pressure. The water is expelled from irrigating tube 16 through an aperture 19 or a series of apertures located at free end 17 and into the intestine. The abutment of spacing cup 21 against the skin of the user prevents any unnecessary leakage of water from the irrigating tube 16 at this stage.

Figure 5:
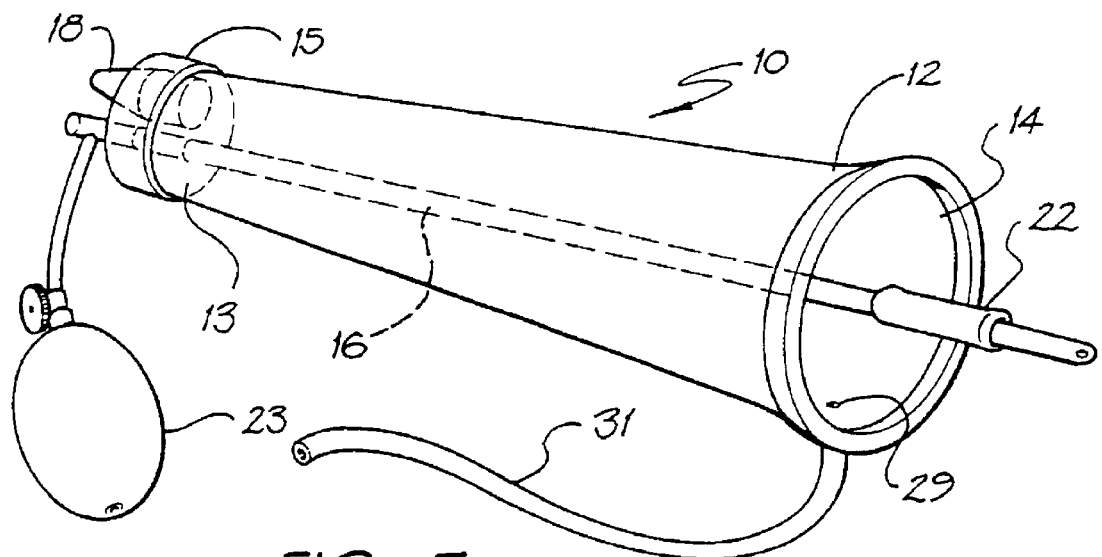
FIG. 5 is a perspective view of a third embodiment of the invention.
Figure 6:
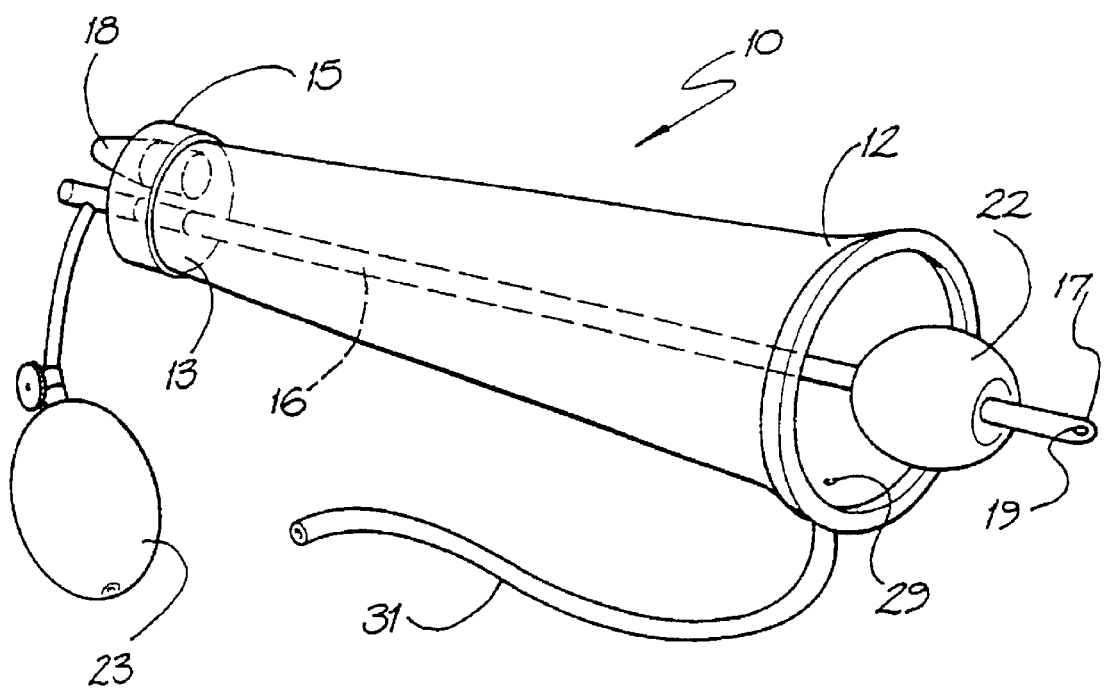
FIG. 6 is a further perspective view of the embodiment of the invention depicted in FIG. 5.

In another embodiment of the invention, depicted in FIGS. 5 and 6, the irrigating tube 16 is provided with a balloon 22 adjacent free end 17. In this embodiment it may be preferable that the irrigating tube 16 has two internal lumenae, one to provide water to the free end 17 and the other to provide air to the balloon 22. Air may be pumped through one of the lumen by way of application of force to a hand held pump 23 connected to that lumen adjacent the outlet 15. When the free end 17 of irrigating tube 16 is in situ within the intestine of a user, the balloon 22 is inflated such that it substantially seals with the wall of the orifice of a user and prevents any excessive loss of water from the orifice in addition to preventing relative movement of the irrigating tube 16 to the orifice.

In this embodiment the inlet 14 is again placed against the skin of the user about the stoma or other bodily orifice and air drawn out of the main chamber 11 through a funnel 18 attached to or integral with outlet 15. Once a small quantity of air is evacuated from the main chamber 11, the inlet 14 forms a suction seal with the skin surrounding the orifice of the user. When the inlet 14 is brought into sealing contact with the skin of a user, the irrigating tube 16 is moved into the bodily orifice such that it is positioned internal the intestine of the user. Once free end 17 is in situ within the intestine, the balloon 22, which is also positioned internal the intestine, is inflated such that it forms a seal around the bodily orifice. Water may then be introduced into the intestine through the irrigating tube 16 via aperture 19 or a series of apertures located at free end 17. The inflation of balloon 22 around the bodily orifice prevents any unnecessary leakage of water from the irrigating tube 16 at this stage.

Figure 7:
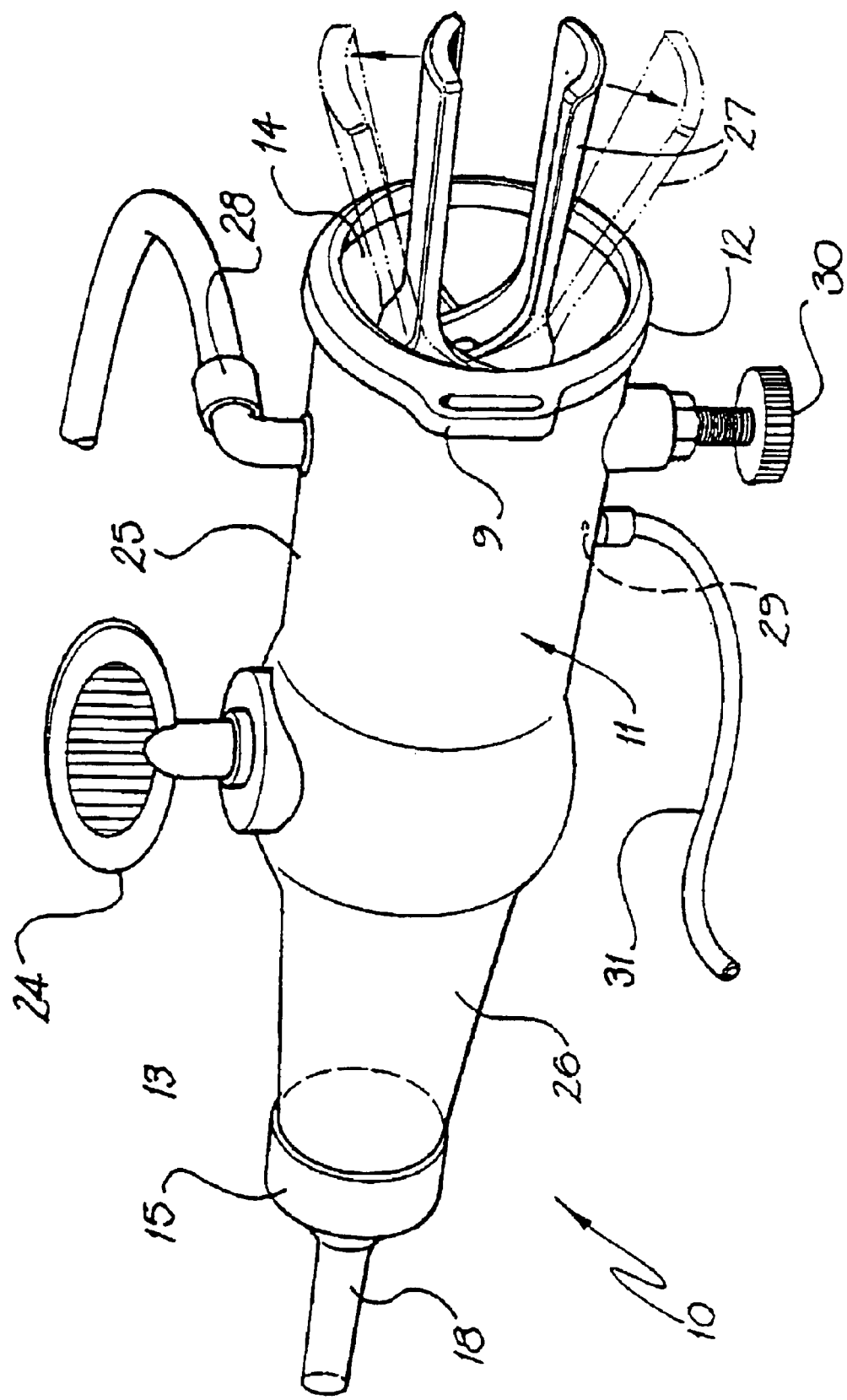
FIG. 7 is a perspective view of a fourth embodiment of the invention.
Figure 8:
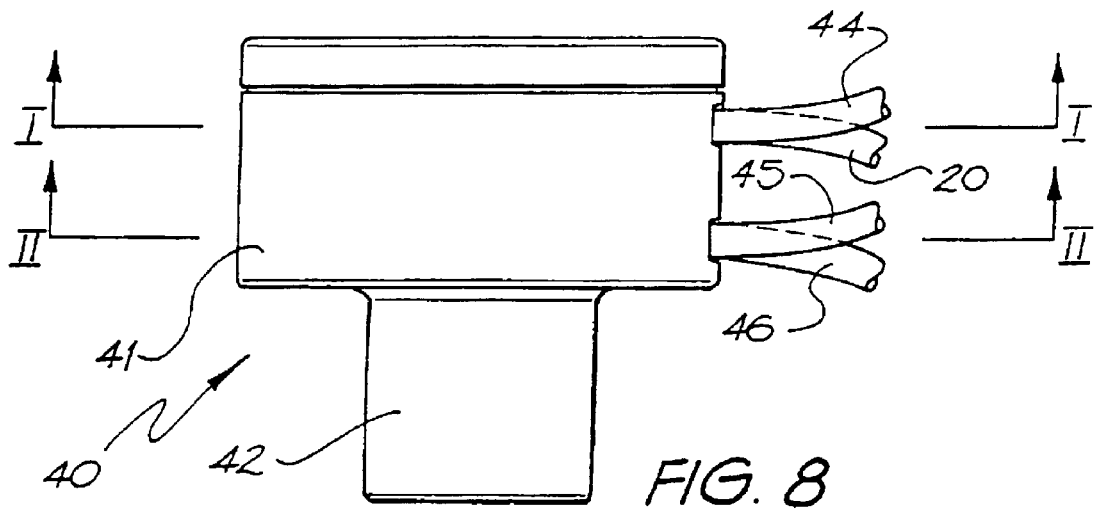
FIG. 8 is a side elevational view of a dual-action peristaltic pump for use in the present invention.
Figure 9:
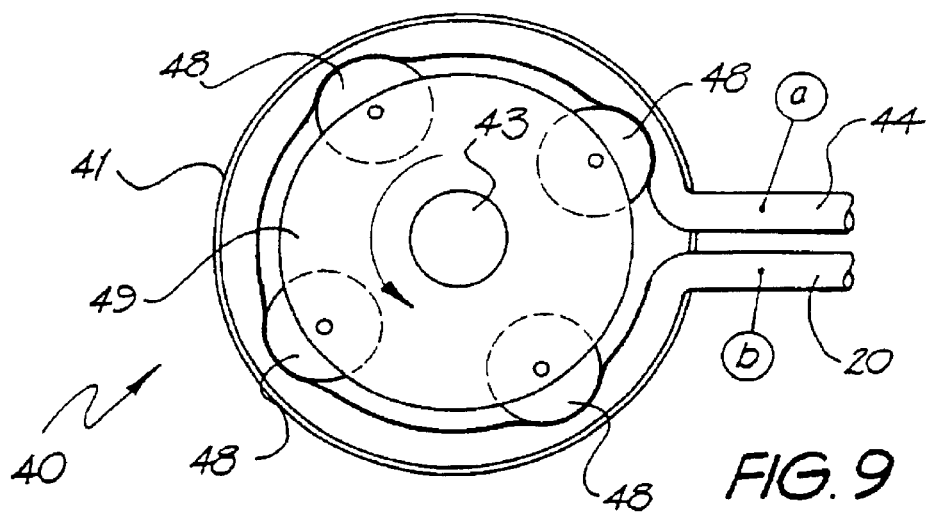
FIG. 9 is a cross-sectional view of the pump of FIG. 8 viewed along line I—I.
Figure 10:
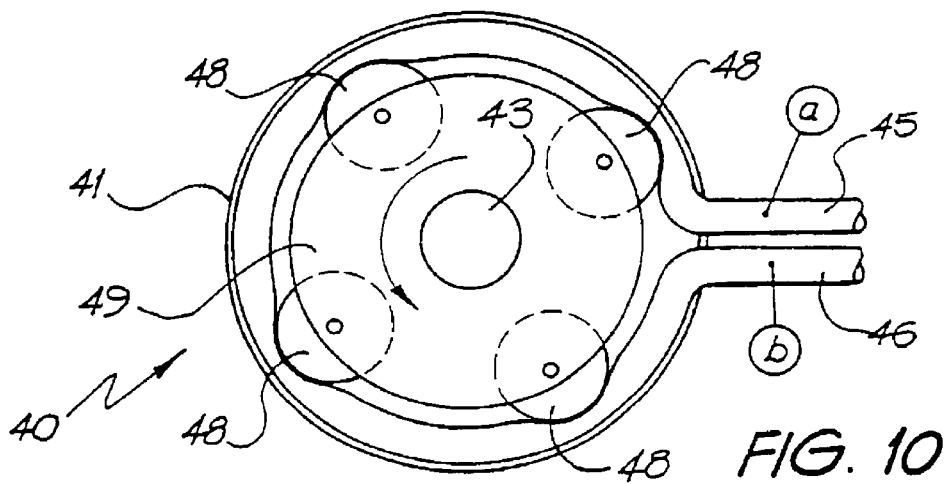
FIG. 10 is a cross-sectional view of the pump of FIG. 8 viewed along line II—II.

In another embodiment of the invention depicted in FIG. 7, the device 10 again comprises a main chamber 11 having two ends 12 and 13. An inlet 14 is located at end 12 and an outlet 15 positioned at end 13. A valve 24 is positioned about midway along the main chamber 11 such that the main chamber 11 is dividable into two separate compartments, first compartment 25 and second compartment 26. Extending from the first compartment 25 is an articulated jaw 27 which in use can be adjusted from a collapsed position to an expanded position (shown in phantom). In use, the device 10 is placed against the skin of a user and the inlet 14 caused to form a seal around the orifice of the user. The articulated jaw 27 extends into the orifice in its collapsed position and is subsequently adjusted to its expanded position. In its expanded position, the articulated jaw 27 engages with the wall of the intestine thereby preventing any leakage of waste material from the intestine. Preferably the articulated jaw 27 is encased within a substantially cylindrical and non-rigid sleeve such that when the articulated jaw is in an expanded position, the sleeve forms a tubular area which engages with the wall of the intestine of a user. The articulated jaw may be moved from a first collapsed position to a second expanded position by way of, for example, an adjusting device 30 connected to the articulated jaw 27 through a wall of main chamber 11.

Once the articulated jaw 27 is in position within the intestine and with valve 24 in a closed position, water is introduced into the first compartment 25 through a water inlet 28. The water inlet 28 is preferably connected to a water source, such as a mains tap or portable container (not shown), by way of tubing. The water in the first compartment 25 moves through the first compartment 25 and into the intestine. Again, typically 1–2 liters of water is introduced into the intestine (although not necessarily all at one time) at which point, valve 24 is opened and the water and waste material from the intestine is drawn into the second compartment 26 under the action of a suction pump. From the second compartment 26, the water and waste material is drawn through outlet 15 and into a suitable waste receptacle.

In each embodiment, the main chamber 11 preferably comprises a further control orifice 29, formed at either the first end 12 or the second end 13. The control orifice 29 may be connected to an open-ended tube 31. The function of the control orifice 29 is to prevent excessive suction of inlet 14 with the skin as such suction may cause unnecessary discomfort to a user.

In use, a user places a finger over the open end of tube 31 whilst air is withdrawn from main chamber 11. Should the resulting suction force be too great, a user may remove their finger from the end of tube 31 thereby allowing air to enter main chamber 11. The entry of air into main chamber 11 will vent the main chamber 11 thereby abolishing the suction force previously created. It may be preferable that, rather than using one's finger, the orifice 29 could be sealed by a pressure release valve (not shown). Such a valve could be designed to vent the main chamber 11 should the pressure level within the main chamber 11 fall below a pre-set level.

In each embodiment, the main chamber 11 can include at least one lug 9 adapted to be connected to a belt, strap or other means of holding the main chamber 11 to the body of a user. Preferably, the main chamber 11 has two oppositely disposed lugs 9 at or adjacent inlet 14 to which the respective ends of a belt are attached. In use, the belt is passed around the abdomen and is preferably adjustable or sufficiently elastic to hold the main chamber 11 in place against the body of the user.

In each embodiment of the invention, suction may be applied to the device 10 either during the step of irrigation or following irrigation. Furthermore, a user may introduce only a limited volume of water, for example 0.5 liters to the intestine at first instance. The introduction of a preliminary volume of water stimulates the intestine to commence evacuation of waste material. Further volumes of water may then be introduced into the intestine at varying time intervals to irrigate the intestine and to remove further waste material. In this way, removal of waste is facilitated both by the natural movements of the intestine as well as by irrigation of the bowel. Additional suction will, of course, further facilitate removal of waste material from the intestine.

In a further embodiment of the invention as depicted in FIGS. 8 to 12, device 10 may be connected to a dual-action peristaltic pump 40. The pump 40 comprises a housing 41 and a motor 42. The pump 40 further comprises one or more rollers 48 mounted on a disc 49 adapted to rotate within the housing 41. The rotation of the disc 49 is provided by a central drive shaft 43 which is rotated by motor 42. The motor 42 can be mains powered or powered by a battery. Located on a side of the housing 41 is an inlet (a) and an outlet (b). In a preferred embodiment, inlet (a) and outlet (b) are simply slots in the side of the housing 41. Tubing 44 is connected to a water source and is adapted to pass through inlet (a), around the housing 41, between the rollers 48 and the wall of the housing 41, and out through outlet (b). As tubing 44 leaves the housing 41 through outlet (b) it connects with or is preferably integral with tubing 20 which in turn connects with the irrigating tube 16 of device 10.

Similarly, tubing 45 extends from funnel 18 of device 10 and carries waste material from the intestine through inlet (a) of housing 41. The tubing 45 is disposed immediately below tubing 44 in the housing 41. Again tubing 45 is adapted to pass through inlet (a), around the housing 41, between the rollers 48 and the wall of the housing 41, and out through outlet (b) where it is connected to or preferably integral with tubing 46 which transports the waste matter to a suitable receptacle such as a toilet.

In use, motor 42 causes rotation of the central drive shaft 43 which in turn causes rotation of disc 49. On rotation of disc 49, the rollers 48 compress tubes 44 and 45 against the wall of the main body 41. Any contents of the tubes 44 and 45 will therefore be squeezed through the tubes from inlet (a) to outlet (b). Accordingly, the water content of tubing 44 is squeezed through the pump 40 and ultimately into device 10 via tube 20. Similarly, the waste matter content of tubing 45 is passed through funnel 18 of device 10 and is squeezed through pump 40 and ultimately into a suitable receptacle via tubing 46.

In the embodiment of the invention depicted in FIG. 11, the pump 40 is shown attached to device 10. Water from a water source passes through tubing 44 and through pump 40. The water exits the pump via outlet (b) and is carried through tube 20 to irrigating tube 16. Irrigating tube 16 in turn is extendable into the bodily orifice of a user and water passing through irrigating tube 16 is introduced into the intestine of a user through aperture 19. Once the step of irrigating the intestine has been completed and the irrigating tube 16 withdrawn into the main chamber 11 of device 10, the exit of waste matter from the intestine commences. Indeed, as in the embodiment depicted in FIG. 1, as there is no balloon 22 or spacing cup 21 it can be envisaged that waste matter will exit the orifice and into the main chamber 11 prior to withdrawal of irrigating tube 16. As previously described it may be desirable to leave water flowing through the irrigating tube 16 at this stage to aid flushing of waste material into the pump 40 and ultimately into a suitable receptacle. With the pump 40 activated, any waste material collected in the main chamber 11 of device 10 is caused to exit via funnel 18. The waste material then passes through tubing 45 and through pump 40. Upon exiting the pump 40, tubing 45 connects or is integral with tubing 46 which carries the waste material to a suitable receptacle, for example, a toilet.

Figure 12:
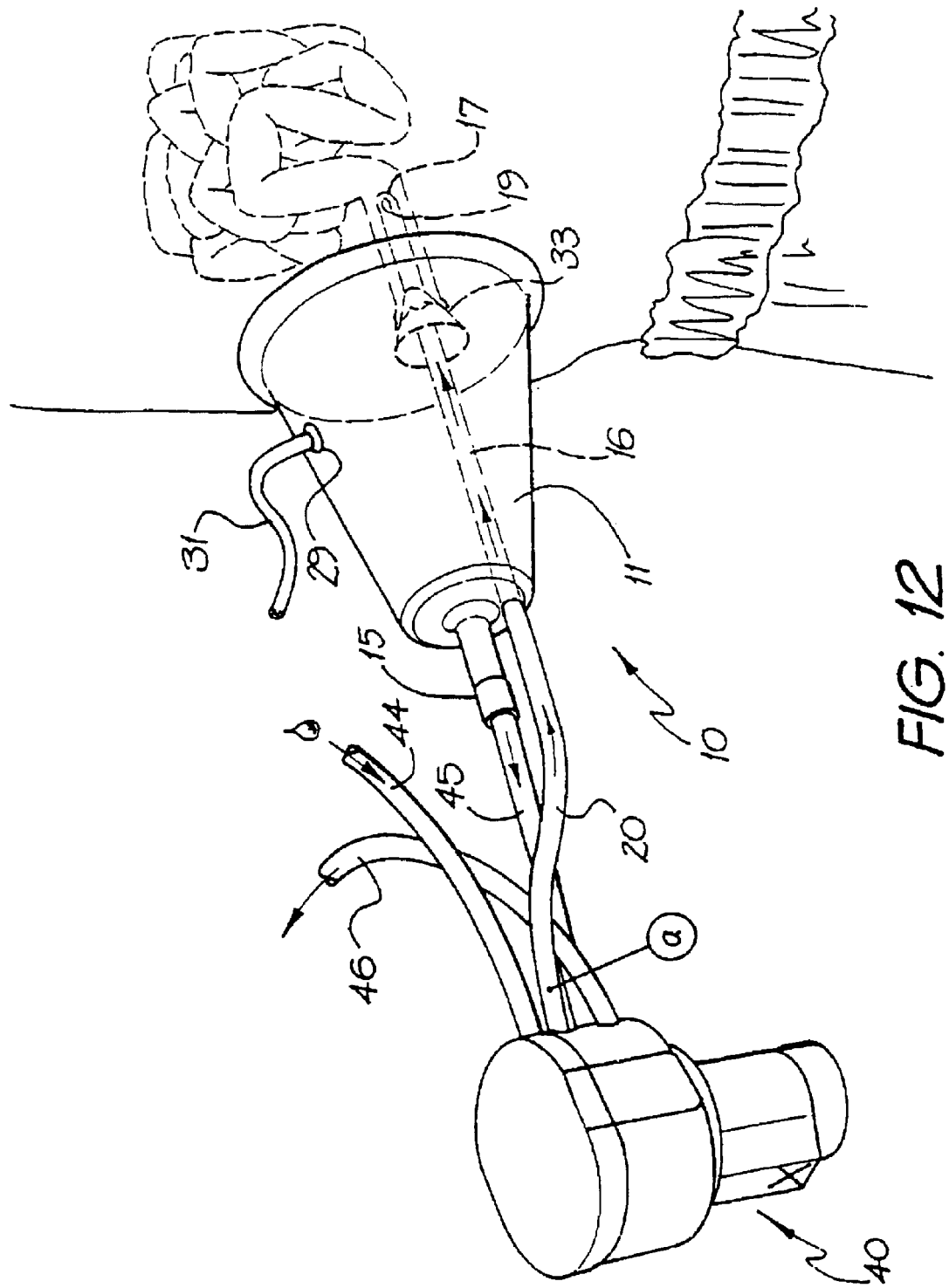
FIG. 12 illustrates use of a further embodiment of the device according to the invention.

In the embodiment of the invention depicted in FIG. 12, the main chamber 11 is bell-shaped. In this embodiment, instead of end 20 connecting with irrigating tube 16 through outlet 15, end 20 passes directly through the wall of the main chamber wherein it connects with or is integral with irrigating tube 16.

As depicted in FIG. 12, the free end 17 of irrigating tube 16 is provided with a cone 33 that increases in diameter away from the free end 17. The cone 33 can be formed from a polymeric or elastomeric material and serves to seal the orifice about the irrigating tube 16 when it is inserted into the orifice. The increasing diameter of the wall of the cone 33 serves to ensure that the irrigating tube 16 cannot be inadvertently inserted too far into the orifice.

While the suction means and pumping means can be a single pump means it will be envisaged that separate devices could be utilised to provide these components of the systems according to the present invention. For example, manually and mechanically operable piston-type and impeller-type pumps could be utilised as suction means to draw waste product from the chamber. Individual peristaltic pumps could also be utilised to both force irrigating fluid through the irrigating means and draw waste product from at least the chamber.

Whichever type of pump is utilised in association with the device or in the systems defined herein, the pump will operate to provide suction within medically approved ranges. The housing and componentry of the pumps can be constructed of any suitable material, such as polytetrafluoroethylene (PTFE).

Figure 13:
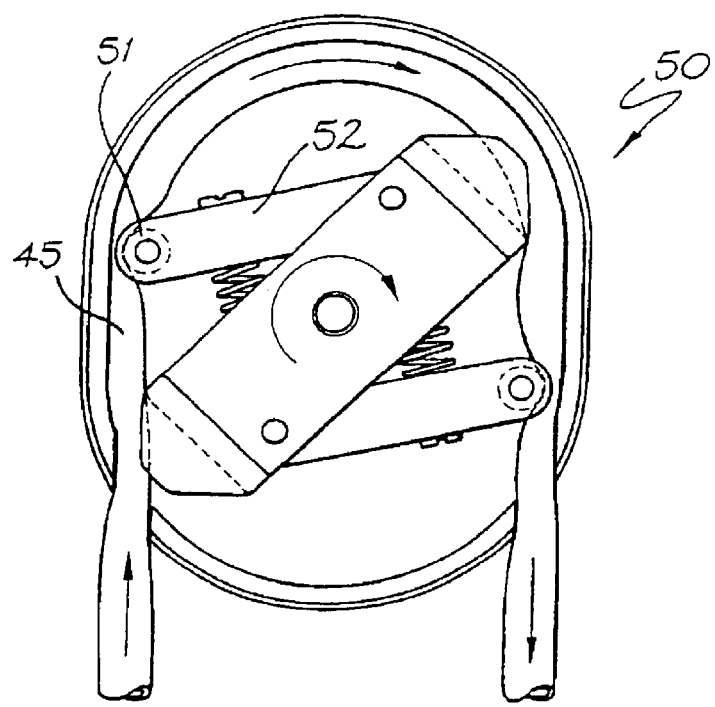
FIG. 13 depicts a plan view of a single-action peristaltic pump, with its cover removed, that can be used to draw waste product from the device according to the present invention.

While a dual action peristaltic pump as described above is preferred, other pump means can be utilised in association the device according to the present invention. For example, a single action peristaltic pump 50 can be utilised to draw waste through and from the main chamber 11 of device 10. An example of the type of peristaltic pump is shown in FIG. 13, in which the waste product to be transported away from the main chamber 11 is forced by rollers 51, which rotate on the arms 52, through the flexible tubing 45, as the rollers 51 force the tubing 45 against the wall of the pump as they rotate around the pump. This embodiment has the advantage in that the waste product being evacuated is separated from the rotor of the pump, and that the tubing 45 can easily be cleaned by flushing or easily and cheaply replaced.

Figure 14:
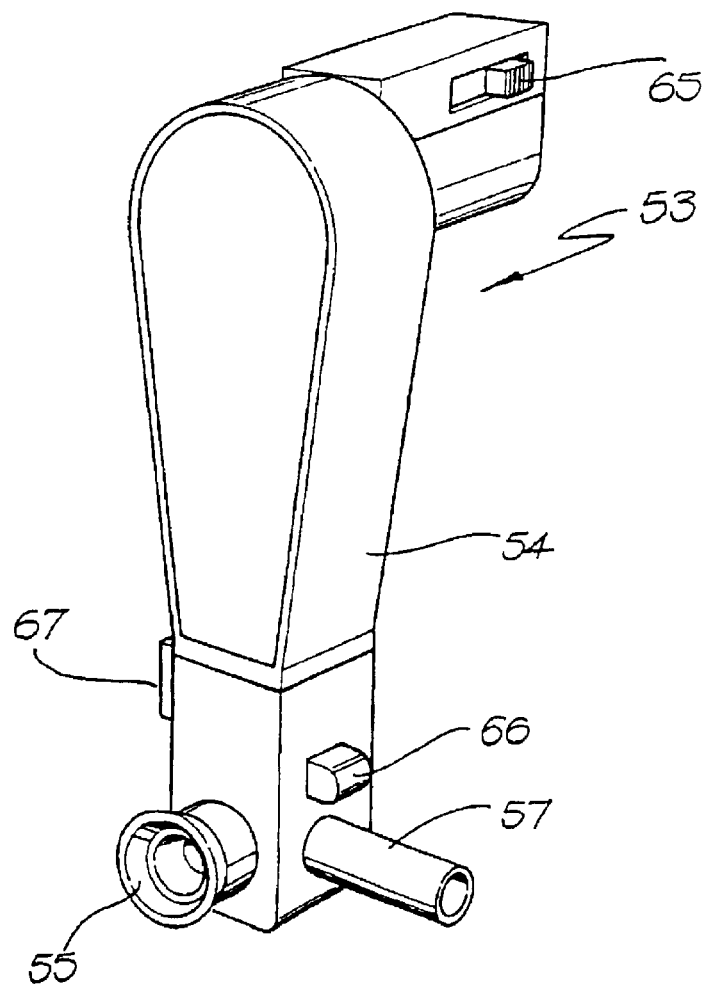
FIG. 14 is a perspective view of another type of pump for use with the present invention.
Figure 15:
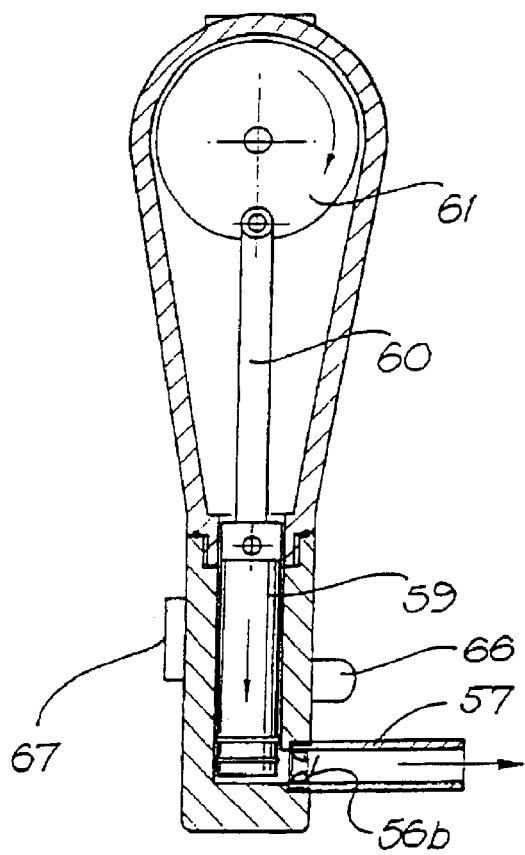
FIGS. 15 and 16 are sectional views of the pump depicted in FIG. 13.
Figure 16:
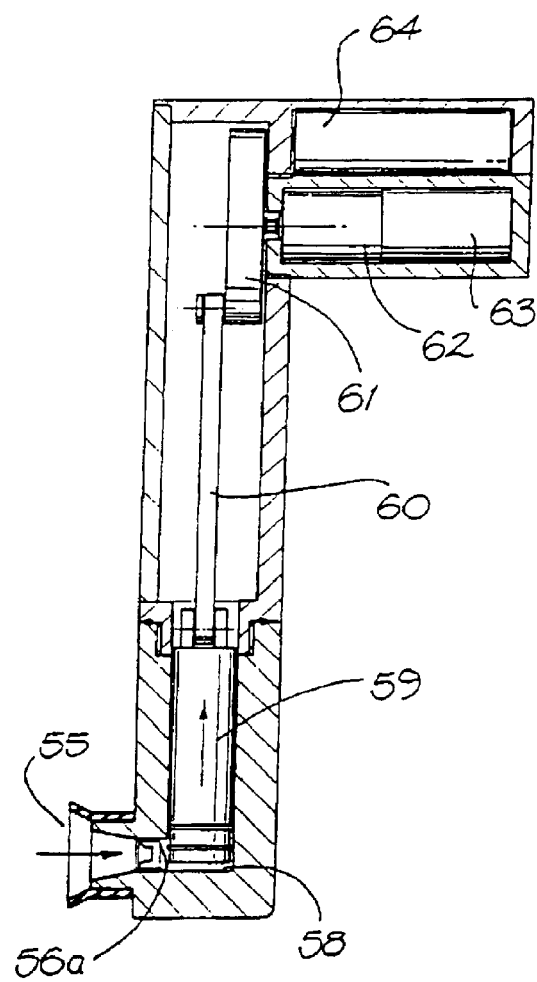

Other non-peristaltic type pumps can be utilised to draw waste products from the main chamber 11 of device 10. One example is the battery operated pump 53 shown in FIGS. 14 to 16. The pump 53 comprises a hand held body 54, having an inlet 55 with a non return inlet valve 56a of any suitable type, and an outlet 57 with a non return discharge valve 56b of any suitable type. Both the inlet 55 and the outlet 57 are in communication with the cylinder chamber 58. A drive piston 59 is slidably mounted in the cylinder chamber 58, and forms a labyrinth seal with the cylinder wall. A connecting rod 60 is pivotally connected, at one end, to the piston 59 and at the other end to a fly wheel 61. The fly wheel 61 is connected via a gear box 62 to an electric motor 63, which is powered by the battery 64.

To use the pump 53, a user first connects the inlet 55 of the pump 53 into sealing engagement with the tubing 45 extending from outlet 18 of the chamber 11, and operates the switch 65. The piston 59 reciprocates along the cylinder 58 as the fly wheel 61 rotates, whereby during the suction stroke, the outlet valve 56b is closed and the inlet valve 56a is open and waste material is drawn from the main chamber 11 into the cylinder chamber 58, and when the piston 59 moves in the discharge stroke, the inlet valve 56a closes and the outlet valve 56b opens, whereby the waste drawn into the cylinder chamber 58 is discharged through the outlet 57 and into a device for receiving the waste, such as a toilet. The pumping is continued until sufficient waste has been evacuated through the main chamber 11.

A hand stop 66 is located on the hand held body 54, to assist in the useability of the pump and a potentiometer 67 is located on the hand held body 54 to vary the speed of the motor and hence the suction head.

In a variation of the pump of this embodiment (not shown), the outlet 57 is aligned with the cylinder chamber 58 and has the same internal diameter. To assist in cleaning of the pump, a lining tube is inserted into the cylinder chamber 58 to form a lining along which the piston 59 moves and also which forms a flexible outlet of any required length.

Figure 17:
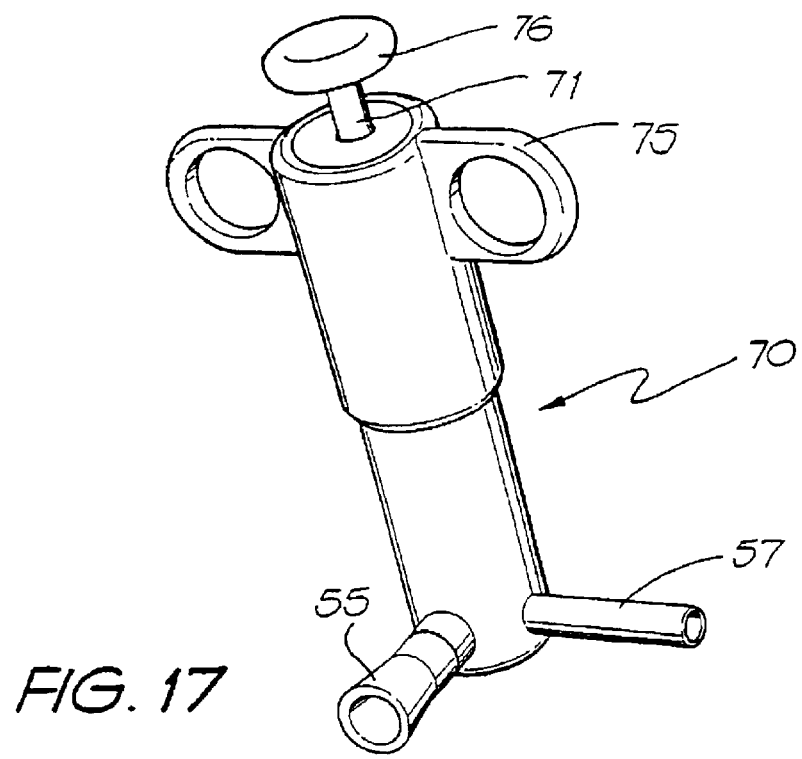
FIG. 17 is a perspective view of another type of pump for use with the present invention.
Figure 18:
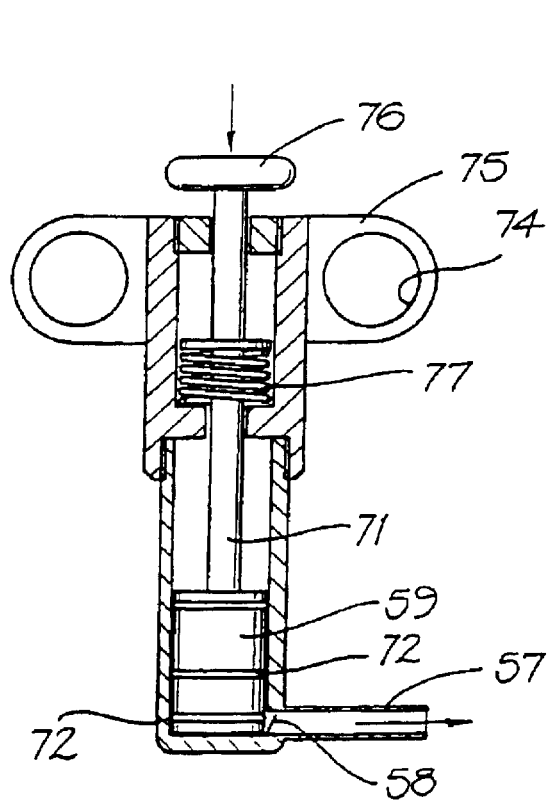
FIGS. 18 and 19 are sectional views of the pump depicted in FIG. 16.
Figure 19:
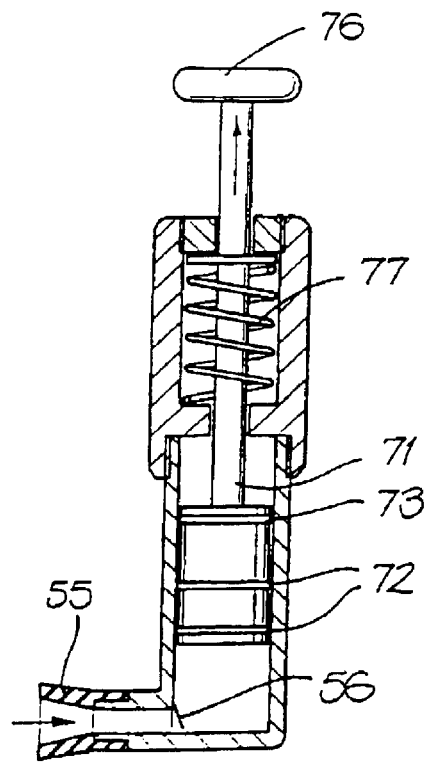

Another embodiment, in the form of a manually activated pump, is shown in FIGS. 17–19. This pump 70 operates in a similar manner to that of the battery operated pump, described previously.

However the piston 59 is operated manually. A drive shaft 71 is connected to the piston 59, which has, as seals, a system of two elastomeric O-rings 72 and a nylon or similar plastics O-ring 73 located in respective grooves around the piston 59.

To use the pump 70, a user places a finger (not shown) in the openings 74 in the wings 75, and depresses the head 76 of the drive shaft 71 driving the piston 79 in the discharge stroke, against the spring means 77. When the head 76 is released, the spring means 77 moves the piston 59 in this suction stroke. Conversely the head 76 could be pulled to provide the suction stroke with the spring means 77 supplying the discharge stroke.

A pump according to a further embodiment of the present invention is shown in FIGS. 20–22. This pump 80 comprises a hand held body 81, having located at one end an inlet/outlet 82 and an outlet/inlet 83, both the inlet and the outlet are in communication with a circular cavity 84; the inlet and outlets 82, 83 are in the form of pipes 85, 86. An impeller 87 having a plurality of radially extending vanes 88 is mounted therein in sealing engagement with the wall of the circular cavity 84. The pump 80 is controlled by a bi-directional motor 89, with a forward or reverse switch 90.

To use the pump 80, a user firstly places the inlet/outlet 82 of the pump 80 into sealing engagement with the tubing 45 extending from funnel 18 of the main chamber 11 and operates the switch 90 drawing waste product from the main chamber 11 by rotating impeller 87 and discharging it through the outlet/inlet 83. The pumping is continued until sufficient waste has been evacuated from the main chamber 11. If desired, such a pump 80 can also be used to pump water or a stool softening fluid through the irrigating catheter 16 and into the bodily orifice.

A potentiometer can be located on the pumps described herein to vary the speed of the motor and hence the suction head. The pumps are so designed to operate within medically approved pressure ranges. Preferably the pumps are waterproof and can be constructed of any suitable material, such as polytetrafluoroethylene (PTFE).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A device for evacuating waste product through an orifice in a mammalian body, the device including a chamber having an inlet and an outlet, the inlet being able to be brought into abutment with the body over the orifice and the outlet being connectable to a suction means adapted to apply suction to the orifice, the device further including an irrigating means for introducing an irrigating fluid into the orifice, the irrigating means having a free end that is movable relative to the chamber between at least a first position outside the orifice and a second position at least partially within the orifice.

2. A device for evacuating waste product through an orifice in a mammalian body, the device including a chamber having an inlet and an outlet, the inlet being able to be brought into abutment with the body over the orifice and the outlet being connectable to a suction means adapted to apply suction to the orifice, and an orifice engaging means that is insertable within the bodily orifice and substantially seals said bodily orifice when the inlet of the chamber is in abutment with the body.

3. The device of claim 1 or claim 2 wherein the inlet of the chamber seals with the body about the orifice.

4. A device for evacuating waste product through an orifice in a mammalian body, the device including a chamber having an inlet and an outlet, the inlet being able to be brought into abutment with the body about the orifice and the outlet being connectable to a suction means, the device further including an irrigating means for introducing an irrigating fluid into the orifice, the irrigating means having a free end that is movable relative to the chamber between at least a first position outside the orifice and a second position at least partially within the orifice, wherein the inlet is located at a first end of the chamber and the outlet of the chamber is located at a second end of the chamber distal the first end.

5. The device of claim 4 wherein the outlet comprises an opening in the second end of the chamber.

6. The device of claim 5 wherein the opening is surrounded by a spout extending outwardly from the second end and having a central bore in fluid communication with the opening.

7. The device of claim 1 or claim 2 wherein the chamber has a further orifice formed therein to allow pressure equalisation between the interior and exterior of the chamber.

8. The device of claim 7 wherein the further orifice is formed in a wall of the chamber and wherein the further orifice has an open-ended tube connected thereto.

9. The device of claim 1 wherein the irrigating means comprises a catheter having at least one lumen in fluid communication with an orifice for the passage of an irrigation fluid and a free end for insertion into the bodily orifice of a user.

10. The device of claim 9 wherein the catheter extends through an opening in the outlet of the chamber, and further, wherein the catheter is movable relative to the outlet while also retaining a substantial seal with the opening in the outlet.

11. The device of claim 9 wherein the catheter further includes an orifice engaging member that is engagable with the wall of the orifice in the mammalian body when the catheter is in the second position relative to the chamber.

12. The device of claim 11 wherein the orifice engaging member is an expandable member positioned adjacent the free end of the catheter, the orifice engaging member being able to be expanded when the catheter is in the second position within the bodily orifice.

13. The device of claim 12 wherein the expandable member comprises a balloon member that is inflatable by passing a fluid through the catheter to expand the balloon member.

14. The device of claim 13 wherein the balloon member is in fluid communication with a separate lumen within the catheter and wherein a small quantity of air or another fluid is injected into the separate lumen to cause the balloon member to expand.

15. The device of claim 13 wherein the expansion of the balloon member occludes the bodily orifice about the catheter thereby preventing relative movement of the catheter to the bodily orifice.

16. The device of claim 11 wherein the orifice engaging member comprises a frusto-conical member that increases in diameter away from the free end of the catheter such that it seals the orifice about the catheter when it is inserted into the orifice.

17. The device of claim 9 wherein the catheter further includes a spacing member adapted to at least abut the body about and immediately adjacent the bodily orifice when the catheter is in the second position.

18. The device of claim 17 wherein the spacing member comprises a cup that is mounted to the catheter and spaced from its free end and wherein the distance between the free end of the catheter and the spacing member sets the maximum depth of insertion of the free end into the bodily orifice.

19. The device of claim 2 wherein the orifice engaging means is expandable from a collapsed condition to an expanded condition.

20. The device of claim 19 wherein the orifice engaging means further includes a means to introduce an irrigating fluid into the orifice of a patient.

21. The device of claim 19 wherein the orifice engaging means comprises an articulated jaw member.

22. The device of claim 21 wherein the jaw member is encased within a non-rigid and substantially cylindrical sleeve that is movable into abutment with the wall of the bodily orifice on articulation of the jaw into its expanded condition.

23. The device of claim 22 wherein the combination of the jaw member and the sleeve acts as both the means of delivering an irrigating fluid to within the bodily orifice and an outlet for waste exiting the orifice.

24. The device of claim 1 further including a pumping means wherein the pumping means forces the irrigating fluid through the catheter lumen and wherein further, the pumping means regulates the rate of flow of water through the catheter lumen.

25. The device of claim 2 further including a pumping means to pump an irrigating fluid into the chamber and wherein the pumping means regulates the flow of irrigating fluid into the chamber.

26. The device of claim 1 or claim 2 when used in the evacuation of waste product from artificial stomas including colostomies.

27. A method of evacuating waste from an orifice in a mammalian body using the device of claim 1, the method including the steps of:
    (i) abutting the inlet of the chamber to the body about the orifice;
    (ii) moving the irrigating means to the second position where its free end is at least partially within the orifice;
    (iii) irrigating the bodily orifice with an irrigating fluid transported through the irrigating means; and
    (iv) applying suction to the outlet of the chamber to withdraw waste from the orifice into the chamber and through the outlet.

28. The method of claim 27 including the further step of sealingly engaging the free end of the irrigating means with the bodily orifice prior to, and at all times while, the bodily orifice is irrigated with the irrigating fluid.

29. The method of claim 28 wherein the sealing engagement of the free end is provided by an inflatable balloon that occludes the orifice around the irrigating means.

30. The method of claim 27 for the evacuation of waste product from artificial stomas, such as colostomies.

31. The method of claim 27 for evacuation of waste product from natural stomas, such as the anus.

32. A method of evacuating waste product from an orifice in a mammalian body using the device according to claim 2, the method including the steps of:
    (i) abutting the inlet of the chamber to the body about the orifice;
    (ii) engaging the orifice engaging means within the orifice;
    (iii) irrigating the bodily orifice with an irrigating fluid; and
    (iv) applying suction to the outlet of the chamber to withdraw waste from the bodily orifice into the chamber and through the outlet.

33. The method of claim 32 wherein the orifice engaging means is moved from a collapsed condition to an expanded condition to engage the bodily orifice.

34. The method of claim 32 for the evacuation of waste product from artificial stomas, such as colostomies.

35. The method of claim 32 for the evacuation of waste product from natural stomas, such as the anus.

* * * * *